(12) United States Patent
Thornton

(10) Patent No.: US 6,247,926 B1
(45) Date of Patent: Jun. 19, 2001

(54) ORAL APPLIANCE HAVING A BONDING LAYER AND METHODS FOR FITTING AND RELINING SAME

(76) Inventor: W. Keith Thornton, 5524 Edlen, Dallas, TX (US) 75220

( * ) Notice: Subject to any disclaimer, the term of this patent is extended or adjusted under 35 U.S.C. 154(b) by 0 days.

(21) Appl. No.: 09/483,741

(22) Filed: Jan. 17, 2000

(51) Int. Cl.$^7$ .................................................. A61C 9/00

(52) U.S. Cl. ............................................ 433/48; 433/214

(58) Field of Search .............................. 433/48, 34, 37, 433/38, 214

(56) References Cited

U.S. PATENT DOCUMENTS

| | | | |
|---|---|---|---|
| Re. 33,442 | 11/1990 | George | 128/860 |
| Re. 35,339 | 10/1996 | Rapoport | 128/204 |
| 690,663 | 1/1902 | Pratt . | |
| 746,869 | 12/1903 | Moulton . | |
| 774,446 | 11/1904 | Moulton . | |
| 885,196 | 4/1908 | Steil . | |
| 893,213 | 7/1908 | Whiteway . | |

(List continued on next page.)

FOREIGN PATENT DOCUMENTS

| | | |
|---|---|---|
| 78762/94 | 4/1995 | (AU) . |
| 27647/95 | 1/1996 | (AU) . |
| 156627 | 12/1904 | (DE) . |
| 2320501 | 11/1974 | (DE) . |
| 3543931 | 6/1987 | (DE) . |
| 3707952 | 9/1988 | (DE) . |
| 3719009 | 12/1988 | (DE) . |
| 29506512 | 7/1995 | (DE) . |
| 19524534 | 5/1996 | (DE) . |
| 0312368 | 4/1989 | (EP) . |
| 0359135 | 3/1990 | (EP) . |
| 1569129 | 6/1980 | (GB) . |
| WO 98/20924 | 5/1998 | (WO) . |

OTHER PUBLICATIONS

Mayo Clinic Health Letter, vol. 13, No. 7, "Snoring.", Jul. 1995.
Photocopies of 2–piece dental device manufactured by Currie–Gibson Dental Laboratory, Inc. prior to Apr. 13, 1993.
Farrar & McCarty, "A Clinical Outline of Temporomandibular Joint Diagnosis and Treatment," Normandie Study Group for TMJ Dysfunction, 3 pages, 1983.
Professional Positioners brochure, "Dedicated to Excellence," 4 pages, Unknown.
Great Lakes Orthodontics, Ltd., "Nocturnal Airway Patency Appliance™ (NAPA)," General Instructions, 2 pages.
Schmidt–Nowara, et al., "Oral Appliances for the Treatment of Snoring and Obstructive Sleep Apnea: A Review," Sleep, 18(6):501–510.
George, "Treatment of Snoring and Obstructive Sleep Apnea with a Dental Device," General Dentistry, 5 pages.
Database WOI, Section PQ, Week 9039, Derwent Publications, Ltd., London, GB XP–002116355—Abstract "Surgical Mouth Air Duct.", Dec. 15, 1989.
CPAP/PRO®. . . Introducing a New Comfort Level for CPAP Users!! brochure (2 pages), No date.

Primary Examiner—Gene Mancene
Assistant Examiner—Melba Bumgarner
(74) Attorney, Agent, or Firm—Baker Botts L.L.P.

(57) ABSTRACT

An oral appliance (10) includes a bonding layer (22) coupled to a tray (18). A deformable material (20) that includes an aliphatic polyester is coupled to the bonding layer (22). The bonding layer (22) may include a self-curing acrylic material, and the aliphatic polyester may include a polycaprolactone polymer having the formula:

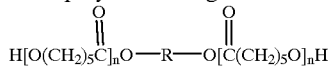

where R is an aliphatic hydrocarbon. The bonding layer (22) may be chemically bonded to the tray (18), and the deformable material (20) may be chemically bonded to the bonding layer (22).

8 Claims, 1 Drawing Sheet

U.S. PATENT DOCUMENTS

| | | | |
|---|---|---|---|
| 1,076,534 | 10/1913 | Wallen . | |
| 1,146,264 | 7/1915 | Kelly . | |
| 1,483,694 | 2/1924 | Stukey . | |
| 1,649,664 | 11/1927 | Carter . | |
| 1,674,336 | 6/1928 | King . | |
| 2,171,695 | 9/1939 | Harper . | |
| 2,178,128 | 10/1939 | Waite | 128/136 |
| 2,383,649 | 8/1945 | Heidbrink | 128/142 |
| 2,424,533 | 7/1947 | Faires | 128/136 |
| 2,521,039 | 9/1950 | Carpenter | 128/136 |
| 2,521,084 | 9/1950 | Oberto | 128/141 |
| 2,531,222 | 11/1950 | Kesling . | |
| 2,574,623 | 11/1951 | Clyde | 128/136 |
| 2,590,118 | 3/1952 | Oddo, Jr. | 128/136 |
| 2,627,268 | 2/1953 | Leppich | 128/136 |
| 2,833,278 | 5/1958 | Ross | 128/136 |
| 2,867,212 | 1/1959 | Nunn, Jr. | 128/136 |
| 2,882,893 | 4/1959 | Godfroy | 128/136 |
| 3,037,501 | 6/1962 | Miller | 128/141 |
| 3,107,668 | 10/1963 | Thompson | 128/136 |
| 3,124,129 | 3/1964 | Grossberg | 128/136 |
| 3,132,647 | 5/1964 | Corniello | 128/136 |
| 3,219,033 | 11/1965 | Wallshein | 128/136 |
| 3,277,892 | 10/1966 | Tepper | 128/172.1 |
| 3,312,216 | 4/1967 | Wallshein | 128/136 |
| 3,321,832 | 5/1967 | Weisberg | 32/32 |
| 3,434,470 | 3/1969 | Strickland | 128/136 |
| 3,457,916 | 7/1969 | Wolicki | 128/136 |
| 3,513,838 | 5/1970 | Foderick et al. | 128/136 |
| 3,522,805 | 8/1970 | Wallshein | 128/136 |
| 3,658,058 | 4/1972 | Neidhart et al. | 128/147 |
| 3,854,208 | 12/1974 | Arant | 32/19 |
| 3,864,832 | 2/1975 | Carlson | 128/136 |
| 3,871,370 | 3/1975 | McDonald | 128/136 |
| 3,884,226 | 5/1975 | Tepper | 128/136 |
| 4,016,650 | 4/1977 | Leusner et al. | 32/17 |
| 4,026,024 | 5/1977 | Tradowsky | 32/19 |
| 4,114,614 | 9/1978 | Kesling | 128/136 |
| 4,169,473 | 10/1979 | Samelson | 128/136 |
| 4,182,312 | 1/1980 | Mushabac | 433/68 |
| 4,227,877 | 10/1980 | Tureaud et al. | 433/37 |
| 4,233,972 | 11/1980 | Hauff et al. | 128/205 |
| 4,289,127 | 9/1981 | Nelson | 128/207.14 |
| 4,304,227 | 12/1981 | Samelson | 128/136 |
| 4,345,592 | 8/1982 | Giorgini et al. | 128/204 |
| 4,345,593 | 8/1982 | Sullivan | 128/204 |
| 4,376,628 | 3/1983 | Aardse | 433/80 |
| 4,382,783 | 5/1983 | Rosenberg | 433/19 |
| 4,392,490 | 7/1983 | Mattingly et al. | 128/202 |
| 4,433,956 | 2/1984 | Witzig | 433/7 |
| 4,439,147 | 3/1984 | Magill et al. | 433/3 |
| 4,439,149 | 3/1984 | Devincenzo | 433/6 |
| 4,470,413 | 9/1984 | Warncke | 128/201.18 |
| 4,495,945 | 1/1985 | Liegner | 128/200.26 |
| 4,505,672 | 3/1985 | Kurz | 433/6 |
| 4,553,549 | 11/1985 | Pope et al. | 128/421 |
| 4,568,280 | 2/1986 | Ahlin | 433/6 |
| 4,569,342 | 2/1986 | von Nostitz | 128/136 |
| 4,593,686 | 6/1986 | Lloyd et al. | 128/136 |
| 4,602,905 | 7/1986 | O'Keefe, III | 433/41 |
| 4,639,220 | 1/1987 | Nara et al. | 433/69 |
| 4,655,213 | 4/1987 | Rapoport et al. | 128/205.25 |
| 4,669,459 | 6/1987 | Spiewak et al. | 128/136 |
| 4,676,240 | 6/1987 | Gardy | 128/207.14 |
| 4,706,683 | 11/1987 | Chilton et al. | 128/654 |
| 4,715,368 | 12/1987 | George | 128/136 |
| 4,773,853 | 9/1988 | Kussick | 433/6 |
| 4,799,500 | 1/1989 | Newbury | 128/859 |
| 4,858,606 | 8/1989 | Hamlin | 128/204 |
| 4,862,903 | 9/1989 | Campbell | 128/861 |
| 4,870,962 | 10/1989 | Sitnik | 128/205 |
| 4,886,056 | 12/1989 | Simpson | 128/201 |
| 4,901,737 | 2/1990 | Toone | 128/848 |
| 4,906,234 | 3/1990 | Voychehovski | 604/79 |
| 4,919,128 | 4/1990 | Kopala et al. | 128/207.18 |
| 4,932,867 | 6/1990 | Ueno | 433/69 |
| 4,955,393 | 9/1990 | Adell | 128/859 |
| 5,003,994 | 4/1991 | Cook | 128/848 |
| 5,018,533 | 5/1991 | Hawkins | 128/848 |
| 5,028,232 | 7/1991 | Snow | 433/24 |
| 5,042,478 | 8/1991 | Kopala et al. | 128/207.18 |
| 5,042,506 | 8/1991 | Liberati | 128/848 |
| 5,046,512 | 9/1991 | Murchie | 128/848 |
| 5,052,409 | 10/1991 | Tepper | 128/859 |
| 5,056,534 | 10/1991 | Wright | 128/848 |
| 5,065,756 | 11/1991 | Rapoport | 128/204 |
| 5,078,600 | 1/1992 | Austin | 433/73 |
| 5,092,346 | 3/1992 | Hays et al. | 128/848 |
| 5,103,838 | 4/1992 | Yousif | 128/859 |
| 5,112,225 | * 5/1992 | Diesso | 433/48 |
| 5,117,816 | 6/1992 | Shapiro et al. | 128/200.24 |
| 5,154,184 | 10/1992 | Alvarez | 128/848 |
| 5,154,609 | 10/1992 | George | 433/68 |
| 5,183,057 | 2/1993 | Syrop et al. | 128/845 |
| 5,188,529 | 2/1993 | Lüth | 433/68 |
| 5,193,532 | 3/1993 | Moa et al. | 128/204 |
| 5,243,971 | 9/1993 | Sullivan et al. | 128/205 |
| 5,245,995 | 9/1993 | Sullivan et al. | 128/204 |
| 5,267,862 | 12/1993 | Parker | 433/215 |
| 5,277,202 | 1/1994 | Hays | 128/848 |
| 5,284,161 | 2/1994 | Karell | 128/848 |
| 5,313,960 | 5/1994 | Tomasi | 128/848 |
| 5,316,020 | 5/1994 | Truffer | 128/848 |
| 5,365,945 | 11/1994 | Halstrom | 128/848 |
| 5,373,859 | 12/1994 | Forney | 128/846 |
| 5,409,017 | 4/1995 | Lowe | 128/848 |
| 5,427,117 | 6/1995 | Thornton | 128/848 |
| 5,456,264 | 10/1995 | Series et al. | 128/725 |
| 5,458,137 | 10/1995 | Axe et al. | 128/204 |
| 5,477,850 | 12/1995 | Zegler et al. | 128/202 |
| 5,503,146 | 4/1996 | Froehlich et al. | 128/204 |
| 5,517,983 | 5/1996 | Deighan et al. | 128/204 |
| 5,537,994 | 7/1996 | Thornton | 128/205 |
| 5,537,999 | 7/1996 | Dearman et al. | 128/205 |
| 5,538,000 | 7/1996 | Rudolph | 128/205 |
| 5,551,419 | 9/1996 | Froehlich et al. | 128/204 |
| 5,558,090 | 9/1996 | James | 128/207.18 |
| 5,560,354 | 10/1996 | Berthon-Jones et al. | 128/205 |
| 5,566,683 | 10/1996 | Thornton | 128/848 |
| 5,592,935 | 1/1997 | Elstran et al. | 128/205 |
| 5,611,485 | 3/1997 | Davis | 239/8 |
| 5,657,751 | 8/1997 | Karr, Jr. | 128/205 |
| 5,657,752 | 8/1997 | Landis et al. | 128/207 |
| 5,676,133 | 10/1997 | Hickle et al. | 128/205 |
| 5,678,567 | 10/1997 | Thornton et al. | 128/848 |
| 5,687,715 | 11/1997 | Landis et al. | 128/207.18 |
| 5,713,349 | 2/1998 | Keaney | 128/204 |
| 5,718,244 | 2/1998 | Thornton | 128/864 |
| 5,718,500 | 2/1998 | Vinci guerra et al. | 2/431 |
| 5,720,280 | 2/1998 | Elstran et al. | 128/205 |
| 5,720,302 | 2/1998 | Belfer | 128/201.26 |
| 5,746,201 | 5/1998 | Kidd | 128/206 |
| 5,752,510 | 5/1998 | Goldstein | 128/207 |
| 5,755,219 | 5/1998 | Thornton | 128/201 |
| 5,769,633 | * 6/1998 | Jacobs et al. | 433/37 |
| 5,807,100 | 9/1998 | Thornton | 433/48 |
| 5,829,441 | 11/1998 | Kidd et al. | 128/848 |
| 5,846,082 | 12/1998 | Thornton | 433/215 |
| 5,847,020 | * 12/1998 | Ibsen et al. | 522/84 |
| 5,887,587 | 3/1999 | Groenke | 128/207 |
| 5,954,048 | 9/1999 | Thornton | 128/201 |
| 5,983,892 | 11/1999 | Thornton | 128/201 |
| 5,988,166 | 11/1999 | Hayek | 128/205 |
| 6,012,455 | 1/2000 | Goldstein | 128/207 |

* cited by examiner

ORAL APPLIANCE HAVING A BONDING LAYER AND METHODS FOR FITTING AND RELINING SAME

TECHNICAL FIELD OF THE INVENTION

This invention relates generally to the field of oral appliances, and more particularly to an oral appliance having a bonding layer and methods for fitting and relining the same.

BACKGROUND OF THE INVENTION

Many oral appliances include a deformable material for forming a mold of some or all of a user's teeth to customize the oral appliance for the user. The deformable material is often placed in a tray before being inserted into the user's mouth. It is often desirable to form a durable mold that properly fits the user's teeth to improve the performance and lengthen the life of the associated oral appliance. Molds that are not durable or do not properly fit the user's teeth may prevent the associated oral appliance from adequately serving the purposes for which they were constructed.

A known technique for forming a mold of a user's teeth includes inserting a tray with a heated deformable material into the user's mouth, pressing the user's teeth into the deformable material, and removing the tray from the user's mouth after the deformable material has cooled. Such techniques may not provide a proper fit, however, due to the tendency of many deformable materials to contract during cooling, thereby expanding the impressions made by the user's teeth. In addition, this technique must often be repeated numerous times before even a marginally adequate fit can be achieved.

Deformable materials used in connection with such techniques may also cool more quickly and display less thermoplasticity at certain temperatures than the clinical professional might desire, thereby limiting the time in which the clinical professional may manipulate the deformable material to form a mold of the user's teeth. Furthermore, molds fitted using such techniques may be less safe for the user due to the increased tendency of the user's teeth to move with respect to a mold that does not properly fit the user's teeth. Moreover, many molds may display insufficient dimensional stability during cooling, hardness, or biocompatibility to function properly in a variety of contexts. In addition, such materials may be difficult or impossible to introduce into the mouth of a user to properly customize an existing mold, limiting the efficiency, economic availability, and effectiveness of techniques associated with these materials.

Even if an adequate fit is achieved through the use of a suitable deformable material, the deformable material may delaminate from the tray in a relatively short period of time, making the oral appliance inoperative thereafter. In addition, if such delamination occurs during use of the oral appliance, the user is inconvenienced and may need to have the oral appliance mended or replaced. In other situations, the user may be injured or be left more prone to injury as a result of such delamination. These and other deficiencies make prior oral appliances inadequate for many applications.

SUMMARY OF THE INVENTION

According to the present invention, disadvantages and problems associated with oral appliances having deformable materials are substantially reduced or eliminated.

According to one embodiment of the present invention, an oral appliance includes a bonding layer coupled to a tray. A deformable material that includes an aliphatic polyester is coupled to the bonding layer. In a more particular embodiment, the bonding layer includes a self-curing acrylic. In another more particular embodiment, the aliphatic polyester is a polycaprolactone polymer having the formula:

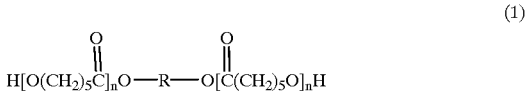

(1)

where R is an aliphatic hydrocarbon. The bonding layer may be chemically bonded to the tray and the deformable material may be chemically bonded to the bonding layer.

According to an additional embodiment of the present invention, a method for fitting an oral appliance to a user includes inserting the oral appliance into the user's mouth and forming a mold of one or more of the user's teeth. The oral appliance includes a bonding layer coupled to a tray and a deformable material that includes an aliphatic polyester coupled to the bonding layer. The oral appliance is inserted into the user's mouth while the deformable material is in a deformable state.

According to another embodiment of the present invention, a method for relining an oral appliance having a first mold of a user's teeth includes coupling a bonding layer to the first mold. A deformable material that includes an aliphatic polyester is coupled to the bonding layer. The oral appliance is inserted into the user's mouth while the deformable material is in a deformable state to form a second mold of one or more of a user's teeth.

An important technical advantage of the present invention includes providing an oral appliance having an improved deformable material to more optimally fit a user's teeth. Improved fit may be important in connection with oral appliances designed to reduce or eliminate trauma injuries or breathing problems such as snoring and sleep apnea. The deformable material of the present invention provides desirable hardness, biocompatibility, dimensional stability during cooling, and thermoplasticity for a variety of applications.

Another important technical advantage of the present invention is providing an oral appliance that enhances the durability and lengthens the useful life of the oral appliance by reducing delamination of the deformable material from the tray. In one embodiment, such delamination is reduced because of the chemical or other bonding between the deformable material and the bonding layer, and between the bonding layer and the tray. Mechanical bonding may contribute to the coupling of the deformable material to the tray to further increase the useful life of the oral appliance.

Other technical advantages are readily apparent to one skilled in the art from the following figures, descriptions and claims.

BRIEF DESCRIPTION OF THE DRAWINGS

For a more complete understanding of the present invention and for further features and advantages thereof, reference is now made to the following description taken in conjunction with the accompanying drawings, in which:

FIG. 1b is a cross-sectional view of the oral appliance shown in FIG. 1a; and

DETAILED DESCRIPTION OF THE INVENTION

Figure 1A:
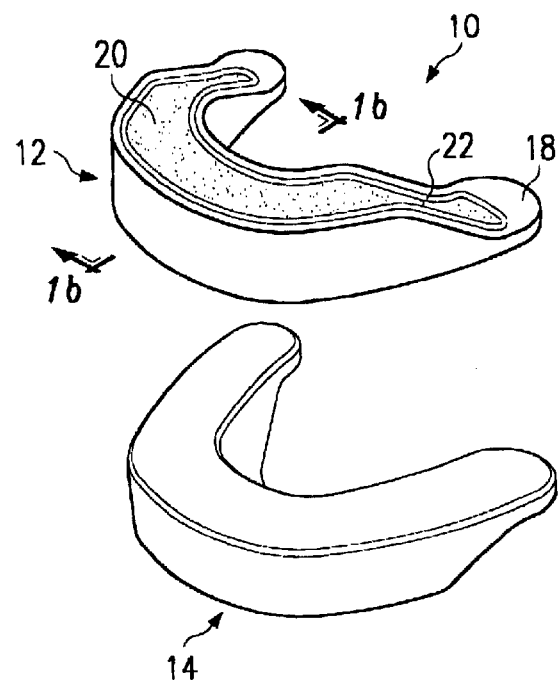
FIG. 1a is a perspective view illustrating an oral appliance having a bonding layer and an improved deformable material.
Figure 1B:
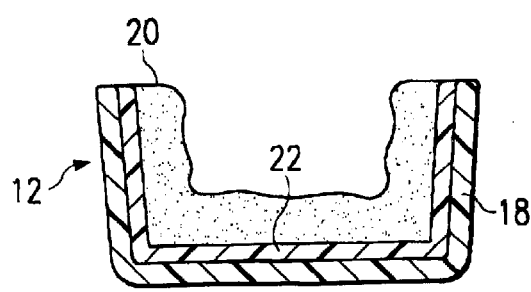

FIG. 1a illustrates an oral appliance 10 that includes an upper arch 12 adapted to receive one or more of a user's upper teeth and a lower arch 14 adapted to receive one or more of the user's lower teeth. When oral appliance 10 is in use, upper arch 12, lower arch 14, or both upper arch 12 and lower arch 14 are inserted into the user's mouth. For convenience, oral appliance 10 will be discussed as including only upper arch 12 unless otherwise indicated. The following discussion applies equally to an oral appliance 10 that includes lower arch 14 instead of, or in addition to, upper arch 12. FIG. 1b is a cross-sectional view of upper arch 12 along the line A—A of FIG. 1a showing additional details of upper arch 12.

Upper arch 12 includes a tray 18 formed from any material suitable for dental uses, many of which are known to those skilled in the art. As an example, methylmethacrylate, a polycarbonate resin thermoplastic such as LEXAN, or any other suitable material maybe used to form tray 18. Tray 18 is adapted to receive a deformable material 20 in which a mold of one or more of the user's upper teeth may be formed. Although tray 18 is shown as being non-customized, tray 18 may itself include a mold of one or more of a user's teeth. For example, tray 18 may be a previously customized oral appliance needing to be relined or otherwise further customized for a particular user. A bonding layer 22, described in greater detail below, couples deformable material 20 to tray 18.

In one embodiment, deformable material 20 includes a polycaprolactone polymer or other aliphatic polyester described in U.S. Pat. Nos. 5,112,225 and 4,784,123, both of which are herein incorporated by reference, as well as in literature distributed by UNION CARBIDE CORPORATION. A polycaprolactone polymer can be combined with other polymers or other suitable materials to form deformable material 20 possessing any number of characteristics, properties, or uses. The present invention contemplates using one or more polycaprolactone polymers or other suitable aliphatic polyesters to replace or combine with methylmethacrylate for any suitable dental application. The polycaprolactone polymer may have the formula:

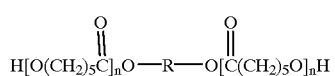 (2)

where R is an aliphatic hydrocarbon and n may range from approximately 300 to approximately 650. The present invention contemplates polycaprolactone polymers having other suitable formulas.

Deformable material 20 may include any suitable polycaprolactone polymer or other aliphatic polyester. For example, and not by way of limitation, the TONE P-700, TONE P-767 or TONE P-787 polycaprolactone polymers manufactured by UNION CARBIDE CORPORATION, taken singly or in any combination, may be used. A suitable light-cured material, another polymer, or any other suitable material, such as a filler, coloring agent, stabilizer, antioxidant, or antimicrobial agent, may be used to replace or combine with a polycaprolactone polymer in forming deformable material 20 possessing any number of characteristics, properties, or uses.

The TONE polycaprolactone polymers are described in U.S. Pat. Nos. 5,112,225 and 4,784,123, and in literature distributed by UNION CARBIDE CORPORATION, as homopolymers, block copolymers, graft copolymers, or other polymers that contain epsilon-caprolactone. Polymerization can be initiated using a diol, for example, and not by way of limitation, ethylene glycol, diethylene glycol, neopentyl glycol, butane diol, hexane diol or any other suitable diol. The diol may have the formula:

$$HO-R-OH \qquad (3)$$

where R is an aliphatic hydrocarbon.

In one embodiment of the present invention, deformable material 20 includes approximately thirty (30) parts by volume TONE P-700 and sixty (60) parts by volume TONE P-767, together with approximately ten (10) parts by volume of one or more other polymers, depending on the application. The present invention contemplates forming deformable material 20 using any suitable mixture or other combination of polycaprolactone polymers, other polymers, and other suitable materials, compounds or compositions.

Deformable material 20 may begin as extruded pellets, beads, or rods of uniform, similar, or differing size, or in other suitable form. Deformable material 20 is heated in a microwave oven, in water or other non-solvent neutral liquid, or in any other suitable manner to between approximately 140 degrees Fahrenheit and approximately 180 degrees Fahrenheit to place deformable material 20 in its deformable state. Deformable material 20 may be kept in a deformable state until the pellets, beads or rods congeal, coalesce or otherwise combine to form a deformable mass capable of assuming a multitude of configurations. Deformable material 20 may be placed in a deformable state before, during, or after deformable material 20 is delivered to tray 18 and coupled to bonding layer 22. The present invention contemplates deformable material 20 mixing, reacting, or otherwise combining with the material of bonding layer 22 while deformable material 20 is in a deformable state.

An important technical advantage of the present invention is the use of bonding layer 22 to couple deformable material 20 to tray 18. In one embodiment, bonding layer 22 is applied to tray 18 before deformable material 20 is placed in tray 18, although the present invention contemplates applying bonding layer 22 directly to deformable material 20 instead of or in addition to tray 18. In a particular embodiment, bonding layer 22 is formed from a self-curing acrylic that includes a suitable mixture of methylmethacrylate and polymethylmethacrylate. The mixture yields a slightly viscous or "runny" liquid at temperatures of interest, which can be poured in a relatively thin layer into tray 18. In one embodiment, bonding layer 22 is approximately one millimeter thick when deformable material 20 is coupled to tray 18, although other suitable thicknesses maybe used.

Without bonding layer 22, delamination of deformable material 20 from tray 18 is more likely to occur, reducing or ending the operative life of oral appliance 10. According to the present invention, bonding layer 22 enhances the durability of oral appliance 10 by reducing or eliminating such delamination, providing an important technical advantage. Bonding layer 22 reduces delamination, at least in part, because it chemically or otherwise adheres deformable material 20 to tray 18. Mechanical bonding, resulting from irregular surfaces of tray 18, deformable material 20, or both, may contribute to the coupling of deformable material 20 to tray 18, but is not required. By incorporating bonding layer 22 according to the present invention, a more durable and effective oral appliance 10 is provided because of, at least in part, its resistance to delamination of deformable material 20 from tray 18.

In one embodiment, oral appliance 10 is formed as follows. Bonding layer 22 is poured into or otherwise applied to tray 18 and deformable material 20 is applied so as to wholly or partially cover bonding layer 22. Due to the chemical compositions of tray 18, bonding layer 22, and deformable material 20, bonding layer 22 chemically or otherwise bonds to both tray 18 and deformable material 20 to secure deformable material 20 to tray 18. Bonding layer 22 may chemically or otherwise bond to tray 18 before, simultaneously with, or after bonding to deformable material 20. As discussed, mechanical bonding may contribute to the coupling of deformable material 20 to tray 18. Once deformable material 20 has been suitably secured to tray 18, construction of upper arch 12 is complete.

To fit oral appliance 10 to a particular user, at least a portion of upper arch 12 including deformable material 20 is heated to place in a deformable state, and upper arch 12 is inserted into the user's mouth, separately from or together with lower arch 14. The user bites down or otherwise presses the user's teeth into deformable material 20 to form a mold of one or more of the user's teeth. Deformable material 20 is then allowed to cool and harden or otherwise take a more permanent shape. These steps may be repeated as many times as necessary or desired to form a mold of one or more of the user's teeth using deformable material 20.

Deformable material 20 cools more slowly and displays thermoplastic properties at lower temperatures than materials such as the ethylene-vinyl acetate copolymer resin ELVAX. This provides the user or a clinical professional with more time to properly conform deformable material 20 to the user's teeth. In addition, deformable material 20 displays increased dimensional stability during the cooling process, relative to ELVAX, which reduces or eliminates fitting problems that might otherwise develop due to the tendency of materials such as ELVAX to contract during cooling, thereby expanding the impressions made by the user's teeth.

Upper arch 12 may remain inserted in the user's mouth or may be removed from the user's mouth before, during, or after deformable material 20 cools. Deformable material 20 maybe formed into amold of the user's teeth in the user's home, in the office of a clinical professional, or in any other suitable location. Formation and fitting of oral appliance 10 may occur in the same or different facilities or other locations, may be performed by the same or different persons, and may be separated by any appropriate length of time. Furthermore, upper arch 12 may be coupled to lower arch 14, a nasal continuous positive air pressure (CPAP) or other suitable mask, or other apparatus to form a device suitable for preventing trauma injuries or treating breathing problems such as snoring and sleep apnea.

Figure 2A:
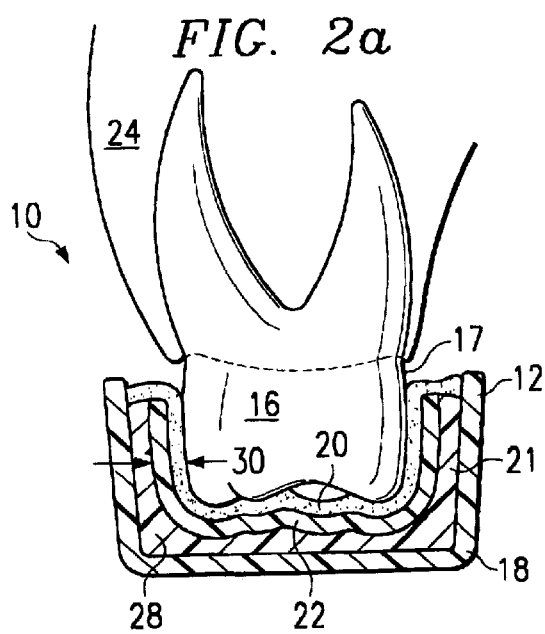
FIGS. 2a and 2b are cross-sectional views illustrating a method for relining an oral appliance using a bonding layer and an improved deformable material.
Figure 2B:
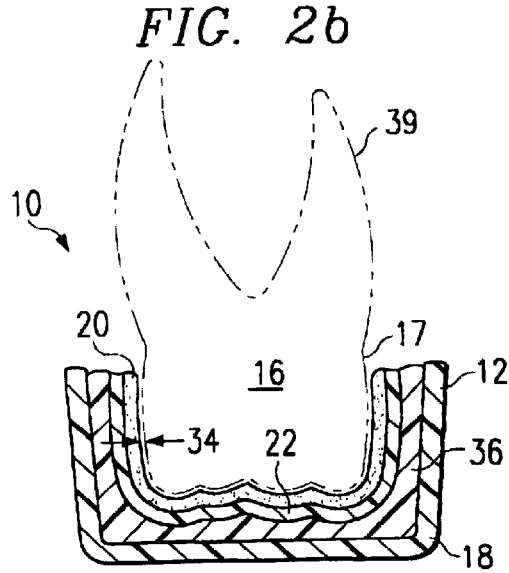

FIGS. 2a and 2b are cross-sectional views illustrating a method for relining an oral appliance 10 using the bonding layer 22 and deformable material 20 discussed above with reference to FIGS. 1a and 1b. Upper arch 12, lower arch 14, or both upper arch 12 and lower arch 14 may be relined using bonding layer 22 and deformable material 20 to more optimally fit the user's teeth. Referring to FIG. 2a, one or more of the user's upper or lower teeth, represented generally by tooth 16, have been pressed or otherwise inserted into some suitable deformable material 21 to form a first mold 28 that resembles the outward surface 17 of tooth 16. Although upper arch 12 is discussed as including first mold 28, the present invention contemplates oral appliance 10 having lower arch 14 instead of, or in addition to, upper arch 12.

Deformable material 21 may include any material suitable for dental applications, for example, the ethylene vinyl copolymer resin ELVAX or one of the polycaprolactone or other polymers discussed above. Deformable material 21 is allowed to cool and harden or otherwise take a more permanent shape. Due to the tendency of materials such as ELVAX to contract during cooling, the impression made by the user's teeth may expand to form first mold 28 that does not optimally fit the user's teeth. Alternatively, first mold 28 may be improperly formed, such that first mold 28 does not optimally fit the user's teeth. A first offset 30 indicates the amount by which first mold 28 is separated from outward surface 17 when tooth 16 is positioned within upper arch 12. The present invention contemplates first mold 28 being an existing oral appliance such as oral appliance 10, a non-customized oral appliance needing customization, or any other suitable mold of one or more of the user's teeth.

To reduce or eliminate first offset 30, bonding layer 22 is coupled to first mold 28 and deformable material 20 is coupled to bonding layer 22, before, simultaneously with, or after bonding layer 22 is coupled to first mold 28. As discussed above, bonding layer 22 chemically or otherwise bonds deformable material 20 and first mold 28 to secure deformable material 20 to first mold 28. According to the present invention, bonding layer 22 enhances the durability of upper arch 12 by reducing or eliminating delamination of deformable material 20 from first mold 28, providing an important technical advantage. Bonding layer 22 reduces such delamination because, at least in part, it chemically or otherwise bonds to both deformable material 20 and first mold 28, thereby securing deformable material 20 to first mold 28. Deformable material 20 may be placed in a deformable state before, during, or after deformable material 20 is coupled to bonding layer 22. Upper arch 12 is then inserted into the user's mouth. The user bites down or otherwise presses the user's teeth into deformable material 20 in order to form a second mold 36 of tooth 16 as shown in FIG. 2b.

As a result, first offset 30 is reduced or eliminated, yielding a second offset 34 that indicates the thickness of the space, if any, between second mold 36 and the outward surface 17 of tooth 16. This results in a relined upper arch 12 that more optimally fits one or more of the user's teeth. Although deformable material 20 may have a tendency to contract as it cools, second offset 34 is smaller than first offset 30. This is due, at least in part, to the dimensional stability displayed by the polycaprolactone polymers as deformable material 20 cools, which reduces the contraction of deformable material 20 during the cooling process. As discussed above, deformable material 20 may cool and harden or otherwise take a more permanent shape relatively slowly and display increased thermoplasticity during cooling, compared to materials such as ELVAX. This may provide the user or clinical professional with additional time to properly conform deformable material 20 to the shape of the user's teeth.

Although deformable material 20 surrounds at least a portion of tooth 16 and couples to bonding layer 22 while deformable material 20 is in a deformable state, the user experiences little or no discomfort when upper arch 12 is inserted into the user's mouth. This is due to a variety of factors, taken separately or in combination. First, since deformable material 20 includes a polycaprolactone polymer, alone or together with any other suitable material, deformable material 20 may transfer relatively little beat to tooth 16 and gum 24 of the user's mouth. Second, since the relining process results in deformable material 20 being delivered in a relatively thin layer to first mold 28, the volume of material transferring heat to tooth 16 and gum 24 of the user's mouth is relatively small. Therefore, the user's mouth may absorb the heat transferred from deformable material 20 with little or no discomfort. Third, tooth 16 and gum 24 of the user's mouth are generally well-adapted to exposure to hot substances, for example, hot food and liquids. The present invention contemplates other factors that may also contribute to the user experiencing little or no discomfort when upper arch 12 is inserted into the user's mouth.

As indicated by the dashed lines 39 in FIG. 2b, upper arch 12 or lower arch 14 may remain inserted in the user's mouth or may be removed from the user's mouth before, during, or after deformable material 20 cools or otherwise hardens to form second mold 36. Once second mold 36 is formed, upper arch 12 maybe repeatedly removed and reinserted into the user's mouth as appropriate for the treatment or other use for which oral appliance 10 was constructed. As discussed previously, bonding layer 22 reduces or prevents delamination of deformable material 20 from first mold 28 to enhance the durability and lengthen the useful life of oral appliance 10. Upper arch 12 may also be coupled to lower arch 14, a nasal CPAP or other suitable mask, or other apparatus to form a device suitable for preventing trauma injuries or treating breathing problems such as snoring and sleep apnea.

Although the present invention is described above in connection with several embodiments, various changes, variations, substitutions, alterations, transformations and modifications can be made hereto without departing from the spirit and scope of the invention as defined by the appended claims.

What is claimed is:

1. A method of relining an oral appliance having a first mold of one or more of a user's teeth, comprising:

coupling a bonding layer to the first mold;

coupling a deformable material to the bonding layer, the deformable material comprising an aliphatic polyester; and inserting the oral appliance in a user's mouth while the deformable material is in a deformable state to form a second mold of one or more of the user's teeth.

2. The method of claim 1, wherein the aliphatic polyester comprises a first polycaprolactone polymer.

3. The method of claim 1, wherein the aliphatic polyester has the formula:

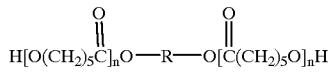

wherein R is an aliphatic hydrocarbon.

4. The method of claim 1, wherein the aliphatic polyester comprises a homopolymer of caprolactone initiated with a diol.

5. The method of claim 1, wherein the deformable material comprises a polymer in addition to the aliphatic polyester.

6. The method of claim 1, wherein the bonding layer comprises a self-curing acrylic material.

7. The method of claim 1, wherein coupling the bonding layer to the first mold comprises chemically bonding the bonding layer to the first mold.

8. The method of claim 1, wherein coupling the deformable material to the bonding layer comprises chemically bonding the deformable material to the bonding layer.

* * * * *